United States Patent [19]

Rennie

[11] 3,939,214

[45] Feb. 17, 1976

[54] OXIDATION OF AROMATIC COMPOUNDS WITH A TETRAVALENT LEAD OXIDATION SYSTEM

[75] Inventor: Robert Allan Campbell Rennie, Runcorn, England

[73] Assignee: Imperial Chemical Industries Limited, London, England

[22] Filed: May 27, 1971

[21] Appl. No.: 147,607

[30] Foreign Application Priority Data
June 8, 1970  United Kingdom............... 27540/70

[52] U.S. Cl...... 260/621 G; 260/289 R; 260/465 F; 260/520; 260/592; 260/618 C; 260/619 R; 260/620; 260/624 R; 260/613 D; 260/623 R; 260/687 H
[51] Int. Cl.$^2$.................. C07C 37/00; C07C 27/16; C07C 49/82; C07D 215/14
[58] Field of Search..... 260/621 G, 283 CN, 287 R, 260/289 R, 405 P, 520, 592, 613 R, 620, 623 R, 624 R, 619 R

[56] References Cited
UNITED STATES PATENTS
2,632,027  3/1953  Smith............................ 260/621 G OTHER PUBLICATIONS
Fieser et al., "Reagents for Organic Synthesis," pp. 550–551, John Wiley & Sons Inc., 1967.
Partch, "J. Am. Chem. Soc.", Vol. 89, pp. 3662–3663, (1967).
Harvey et al., "J. Chem. Soc.", Vol. 1964, pp. 4860–4868, (1964).

Primary Examiner—Norman Morgenstern
Attorney, Agent, or Firm—Cushman, Darby & Cushman

[57] ABSTRACT

The liquid phase oxidation of an aromatic compound comprising a benzene ring having at least one unsubstituted carbon atom to an aromatic compound comprising a hydroxy-substituted benzene ring is effected using as oxidant a solution of a tetravalent lead compound in the presence of a strong acid.

11 Claims, No Drawings

OXIDATION OF AROMATIC COMPOUNDS WITH A TETRAVALENT LEAD OXIDATION SYSTEM

This invention relates to the oxidation of aromatic compounds, and particularly to the liquid phase oxidation of aromatic compounds using a tetravalent lead compound as the oxidising agent.

J. Am. Chem. Soc. 89, 3662 (1967) describes the oxidation of toluene to benzyl alcohol using lead tetrakis (trifluoroacetate) as oxidant. According to the procedure of this article, solid lead tetrakis (trifluoroacetate) is stirred with toluene for 30 minutes, or toluene is added to a mixture of acetic acid, trifluoroacetic anhydride, and red lead oxide ($Pb_3O_4$), and stirred. After alkaline hydrolysis of the product ester, benzyl alcohol was obtained in yields of about 45%, calculated on the basis of initial lead (IV).

We have now discovered that, by working in the absence of solid oxidant, lead (IV) can be used to oxidise the aromatic ring of substituted benzenes, with comparatively little oxidation of the side chain.

According to the present invention, we provide a process for the liquid phase oxidation of aromatic compounds including a benzene ring having at least one unsubtituted carbon atom to aromatic compounds containing a hydroxy-substituted benzene ring, or to the corresponding esters, which process comprises treatment of the aromatic compound with a solution of a tetravalent lead compound in the presence of a strong acid.

By "strong acid," we mean an acid having a pKa value in 0.1 to 0.01 N aqueous solution at ambient temperature numerically less than 1.5 or thereabouts.

Preferred starting materials are alkyl benzenes, such toluene and the xylenes, but the benzene ring may bear other substituents, provided that these are stable to oxidation, and do not interfere, sterically or otherwise, with oxidation of at least one of the carbon atoms of the benzene ring, as may readily be determined by simple experiment. The number and arrangement of substituent groups is immaterial, provided that at least one carbon atom of the benzene ring remains available for oxidation.

In addition to the alkyl benzenes, suitable starting materials include alkoxybenzenes, halobenzenes, diphenyl, or acyl-substituted benzenes. Other convenient substituents of the benzene ring are aryl groups which themselves bear electron-withdrawing substituents, for example carboxyphenyl or cyanophenyl groups. The process of our invention is also applicable to polynuclear aromatic compounds including a benzene ring, for example, naphthalene, anthracene, phenanthrene, quinoline or isoquinoline.

As the initial products of oxidation are esters of substituted hydroxybenzenes, it is desirable that the reaction mixture contains sufficient strong acid, as defined above, to react with all of the initial substrate. Preferably, the sole solvent for the tetravalent lead compound is the strong acid itself or a functional derivative such as the anhydride, but the solution may be diluted with an inert solvent, for example acetic acid or a paraffin or haloparaffin, if required.

The strong acid must be such that tetravalent lead will not precipitate out of the reaction mixture, since it is important to avoid the presence of solid oxidant. Suitable acids thus include perchloric acid and fluoboric acid as well as the several chlorofluoroacetic acids, e.g., dichlorofluoroacetic acid and chlorodifluoroacetic acid but, because of the high solubility of lead tetrakis (trifluoroacetate), trifluoroacetic acid is particularly preferred.

The choice of anion associated with the tetravalent lead compound is not critical, provided that the lead compound can form a homogenous solution in the acid reaction medium. A convenient source of tetravalent lead, because of its ready availability and solubility in strong acids, is lead tetraacetate. As the lead is essential to the reaction, being reduced to the divalent state, it is necessary that a sufficient amount of tetravalent lead be available in the reaction mixture if reaction is to proceed to completion.

The ionic strength of the reaction mixture may advantageously be increased by inclusion of soluble alkali metal salts, e.g., the trifluoroacetates. Lithium and potassium salts have been found to be convenient, in concentrations of about 1 mole per mole of tetravalent lead, though greater or lesser concentrations may be used, up to approximately 5 moles per mole of tetravalent lead.

The reaction temperature is not critical, provided that the reaction mixture remains liquid. Ambient temperature is particularly convenient and is therefore preferred.

The progress of the reaction may be followed by an convenient method, for example, by monitoring the concentration of lead (IV) potentiometrically. Alternatively, samples of the reaction mixture may be withdrawn at intervals and analysed.

After completion of reaction, excess acid, together with cosolvent, if any, may be removed by distillation. Metallic salts present can be dissolved in an aqueous solvent, for example, water or brine, and the product, with or without hydrolysis to the corresponding hydroxy compound, may be recovered by such means as solvent extraction or distillation.

Instead of being hydrolysed, the product esters may be subjected to an ester interchange reaction with another acid, or may be isolated as such.

The lead can be reoxidised to the tetravalent state by conventional means, and re-used for further production of trifluoroacetate esters according to the invention.

For example we have effected re-oxidation of the lead by electrolytic oxidation in acetic acid solution using Pt/Ni electrodes (e.g., at 50°–60°C), separation of the Pb(IV) acetate from the solvent being brought about merely by lowering the temperature of the solution. The solid Pb(IV) acetate deposited is then dissolved in trifluoroacetic acid for use according to the invention.

The oxidation and Pb(IV) regeneration processes may proceed continuously for example by effecting oxidation in a reaction vessel using, say, a lead tetraacetate/trifluoroacetic acid (TFA) oxidising system. After oxidation the mixture is subjected, conveniently in a different vessel, to separation treatment, product being removed, TFA being recycled back to the reaction vessel and the residue containing Pb(II) dissolved, e.g., in acetic acid at 50°C and transferred to the anode compartment of an electrolytic cell where the Pb(II) is converted electrolytically to Pb(IV). After oxidation of the lead to the extent preferably of 10–20% the solution may be transferred to a cooling vessel where the lead tetraacetate crystallises out, to be recycled back to the reaction vessel. The Pb(II) in the supernatant is heat to 50°C again and recycled to the electrolytic cell for further conversion.

It is also possible to carry out electrolytic reoxidation of the lead (II) compound in mixtures of trifluoroacetic acid with either water or acetic acid, such mixtures also being suitable reaction media for oxidation of aromatic substrates by Pb(IV) compounds. Mixtures of trifluoroacetic acid and water containing up to 5% by volume of water, or even up to 10% by volume of water may be suitable as solvents in both the oxidation reaction and the electrolytic regeneration, although 1–2% by volume of water is preferred.

When mixtures of trifluoroacetic acid and acetic acid are used as solvents for both the oxidation reaction and the electrolytic regeneration, it is found that the rate of the oxidation reaction decreases with increasing concentration of acetic acid in the mixture, but that the current efficiency of the electrolytic regeneration tends to increase with increasing concentration of acetic acid in the mixture. The optimum concentration of acetic acid in trifluoroacetic acid will depend upon the reactivity of the substrate to be oxidised, and may be determined by simple experiment. Normally the optimum concentration of acetic acid will not exceed 50% by volume of the mixture of acetic acid and trifluoroacetic acids.

In a system in which the same acid solvent mixture is used for both the oxidation and the electrolytic regeneration steps, both steps may be carried out simultaneously in the same vessel, using only catalytic amounts of lead compound. Thus if the substrate is added to the anode compartment of an electrolytic cell with a porous partition, in which the anode compartment contains a solution of a Pb(II) compound in a suitable solvent mixture optionally including a soluble alkali metal salt and the cathode compartment contains the same mixture without the lead compound, then on electrolysis, the Pb(II) will become oxidised to Pb(IV) which will in turn oxidise the substrate and regenerate Pb(II), thus providing a cyclic process which can be made continuous by the removal of product, recovery of solvent and addition of recycled solvent and new substrate.

The invention is illustrated by the following Examples.

EXAMPLE 1

A reaction vessel was purged with nitrogen and then kept under a nitrogen atmosphere during subsequent operations.

A solution was made up in trifluoroacetic acid of lithium trifluoroacetate (0.286 M) and lead tetraacetate (0.286 M). 0.572 moles of toluene were added per liter of solution, and the mixture was stirred at ambient temperature. The mixture developed a transient intense green colour and then turned brown. Reaction was allowed to continue for 5 minutes, when titration of a sample with potassium iodide and sodium thiosulphate showed complete consumption of lead(IV).

The bulk of the trifluoroacetic acid was removed on a rotary evaporator. The residual syrupy liquid was treated with excess 30% (by weight) sodium hydroxide solution and filtered to remove insoluble salts. The insoluble portion was thoroughly washed with diethyl ether, and the aqueous filtrate was acidified and extracted with diethyl ether. The ethereal extracts were combined and dried over magnesium sulphate, and the ether was removed by evaporation.

Thin-layer chromatography of the residue showed the presence of cresols, and a sample was dissolved in ethyl acetate and analysed by gas-liquid chromatography at 145°C using a 2.4 m column packed with dimethyldioctadecylammonium bentonite ("Bentone 34") and tritolyl phosphate on "Embacel" in a weight ratio of 1:1:10, with 2-phenylethanol as internal standard. ("Bentone" and "Embacel" are Registered Trade Marks).

The yield of cresols, calculated on the basis of initial lead(IV) was 30%. The ratio of p-cresol to o-cresol was 3:5:1, with no detectable amounts of m-cresol and only trace amounts of benzyl alcohol.

The presence of cresols in the product was also confirmed by the mass spectrometry fragmentation pattern of a sample.

EXAMPLE 2

Example 1 was repeated using m-xylene as the starting material (0.572 moles per liter of solution).

The product comprised a mixture of 2,4-xylenol and 2,6-xylenol in a ratio of 4:1, together with some material which is thought to be 3-methylbenzyl alcohol. No 3,5-xylenol could be detected.

EXAMPLE 3

Example 1 was repeated using naphthalene as the starting material. The product comprised a mixture of 1- and 2-naphthols, confirmed by thin layer chromatography with authentic samples, the spots being identified by spraying with diazotised sulphomilic acid.

EXAMPLE 4

Example 1 was repeated using diphenyl as the starting material. The product comprised a mixture of 2- and 4-hydroxydiphenyl, identified by thin layer chromatography.

EXAMPLE 5

Example 1 was repeated using diphenyl ether as starting material. Oxidation occurred, as shown by the formation of Pb(II) compounds.

EXAMPLE 6

Example 1 was repeated, but instead of trifluoroacetic acid, a mixture of chlorofluoroacetic acids obtained by fluorination of trichloroacetic acid, and containing 28% wt. Cl (Cf. 65% Cl in $CCl_3.COOH$) was used. The results were substantially identical to those from Example 1.

EXAMPLE 7

A 0.6 M solution of lithium acetate in anhydrous acetic acid was made by dissolving 6.12g $LiOAc.2H_2O$ and 11.3 ml. of acetic anhydride in glacial acetic acid to make up to 100 cm$^3$. Lead(II) diacetate (24.4g) was dissolved in 75 ml. of the above solution and placed in the anode compartment of an electrolytic cell divided by a porous ceramic separator. The cathode compartment contained 75 ml. of the 0.6 M LiOAc/HOAc solution, the anode was of platinum and the cathode of nickel. The temperature of the cell was maintained at 50°C, and electrolysis carried out at an applied potential of 10v for 270 minutes, giving a current efficiency of 80% and 15% conversion of Pb(II) to Pb(IV). On cooling to 20°C, a solid precipitate (2.7g) was obtained, which on analysis was found to be 97.8% pure $Pb(OAc)_4$.

EXAMPLE 8

Example 7 was repeated, using 100% trifluoroacetic acid in place of acetic acid, 2.0 cm³ of water being added to the solution in the anode compartment.

A current efficiency of 50% was obtained at 15% conversion to Pb(IV). No Pb(IV) compound was precipitated on cooling to 20°C.

EXAMPLE 9

Example 7 was repeated using a mixture of 90% vol. acetic acid and 10% trifluoroacetic acid in place of acetic acid. A current efficiency of 75% was obtained at 15% conversion.

What we claim is:

1. A process for the liquid phase oxidation of an aromatic compound containing a benzene ring with at least one unsubstituted carbon atom to give an aromatic compound containing a hydroxy substituted benzene ring or the corresponding ester, which process comprises treating an aromatic compound selected from the group consisting of alkyl benzenes, diphenyl ether, diphenyl, naphthalene, anthracene, phenanthrene, quinoline and isoquinoline, with a homogeneous solution of a soluble salt of an alkali metal and a tetravalent lead compound dissolved in a strong liquid acid having a pKa less than about 1.5 at a concentration of 0.1 to 0.01 N at ambient temperature whereby said aromatic compound is oxidized to the corresponding hydroxy substituted compound or ester thereof, said strong acid comprising between 50 and 100% by volume of the solution and being selected from the group consisting of perchloric acid, fluoboric acid, trifluoroacetic acid, dichlorofluoroacetic acid and chlorodifluoroacetic acid.

2. A process according to claim 1 wherein the strong acid is trifluoroacetic acid the aromatic compound is toluene or a xylene and the lead compound is lead tetraacetate.

3. A process according to claim 1 wherein the strong acid is a mixture of trifluoroacetic acid and up to 50% by volume of acetic acid.

4. A process according to claim 1 wherein the tetravalent lead compound is initially present in the form of lead tetraacetate.

5. A process according to claim 1 wherein the solution contains from 1 to 5 moles of a soluble salt of an alkali metal for each mole of lead compound.

6. A process according to claim 5 wherein the salt is lithium trifluoroacetate or potassium trifluoroacetate.

7. A process according to claim 1 wherein the aromatic compound is an alkyl benzene containing at least one unsubstituted carbon atom on the benzene ring.

8. A process according to claim 7 wherein the alkyl benzene is toluene.

9. A process according to claim 1 wherein divalent lead compound produced in the reaction is re-oxidized to a tetravalent lead compound.

10. A process according to claim 9 wherein divalent lead compound is oxidized to a tetravalent lead compound by anodic oxidation in an electrolytic cell.

11. A continuous process for the oxidation of an aromatic compound containing a benzene ring with at least one unsubstituted carbon atom which comprises the steps of:

1. contacting an aromatic compound selected from the group consisting of alkyl benzenes, diphenyl ether, diphenyl naphthalene, anthracene, phenanthrene, quinoline and isoquinoline, with a homogeneous solution of a soluble salt of an alkali metal and a tetravalent lead compound dissolved in a strong liquid acid having a pKa less than about 1.5 at a concentration of 0.1 to 0.01 N at ambient temperature whereby said aromatic compound is oxidized to the corresponding hydroxy substituted compound or ester thereof, said strong acid comprising between 50 and 100% by volume of the solution and being selected from the group consisting of perchloric acid, fluoboric acid, trifluoroacetic acid, dichlorofluoroacetic acid and chlorodifluoroacetic acid,
2. removing excess acid by evaporation,
3. isolating the aromatic oxidation product from the residue including divalent lead compound formed in the oxidation,
4. re-cycling the removed acid with fresh aromatic compound to step (1),
5. transferring the divalent lead compound to an electrolytic cell in which the tetravalent compound is regenerated, and,
6. re-cycling the regenerated tetravalent compound to step (1).

* * * * *